(12) United States Patent
Cobb et al.

(10) Patent No.: US 6,506,781 B1
(45) Date of Patent: Jan. 14, 2003

(54) OXAZOLE PPAR ANTAGONIST

(75) Inventors: Jeffrey Edmond Cobb, Durham, NC (US); Millard Hurst Lambert, III, Durham, NC (US); Michael Vance Milburn, Morrisville, NC (US); Barry George Shearer, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/070,474

(22) PCT Filed: Sep. 1, 2000

(86) PCT No.: PCT/US00/24364
§ 371 (c)(1),
(2), (4) Date: Mar. 7, 2002

(87) PCT Pub. No.: WO01/17994
PCT Pub. Date: Mar. 15, 2001

Related U.S. Application Data
(60) Provisional application No. 60/152,761, filed on Sep. 8, 1999, and provisional application No. 60/199,969, filed on Apr. 27, 2000.

(51) Int. Cl.⁷ .................. A61K 31/4245; A61K 31/433; A61K 31/422; C07D 413/12; C07D 417/12
(52) U.S. Cl. ............ 514/363; 514/364; 514/374; 548/131; 548/136; 548/143; 548/235; 548/236
(58) Field of Search ............... 548/131, 136, 548/143, 235, 236; 514/363, 364, 374

(56) References Cited
PUBLICATIONS

Henke, BR., et al: "N–(2–Benzoylphenyl)–L–tyrosine PPAR gamma agonists. 1. Discovery of a novel series of potent antihyperglycemic and antihyperlipidemic agents" Journal of Medicinal Chemistry, vol. 41, No. 25, 1998, pp. 5020–5036, XP000864731.

Oberfield, JL., et al: "A peroxisome proliferator–activated receptor gamma ligand inhibits adipocyte differentiation" Proceedings of the National Academy of Sciences of USA, vol. 96, No. 11, May 25, 1999, pp. 6102–6106, XP002155581.

*Primary Examiner*—Laura L. Stockton
(74) *Attorney, Agent, or Firm*—Robert H. Brink

(57) ABSTRACT

A method is disclosed for rational design of a PPAR, FXR, LXR-alpha, or LXR-beta antagonist comprising chemical modification of a PPAR, FXR, LXR-alpha, or LXR-beta agonist to: a) prevent formation of a hydrogen bond between the agonist and tyrosine or histidine, or tryptophan involved in receptor activation; and/or b) displace the tyrosine or histidine, or tryptophan involved in receptor activation from its agonist bound position. Preferably, little or no additional changes are made in the structure of the agonist so that the resulting antagonist is a close structural analogue of the agonist. Specific examples of PPAR gamma antagonists designed and prepared using the method of this invention are compounds of Formula (I) or (II), or pharmaceutically acceptable salts or solvates thereof, where in Formula (I) X is O, S, or NH; and R is methyl, ethyl, n-propyl, i-propyl, cyclopropyl, n-butyl, phenyl, or —CH$_2$OCH$_3$ and wherein in Formula (II) X is C or N; and R is methyl, ethyl, n-propyl, i-propyl, —CH$_2$OCH$_3$, or —CO$_2$CH$_3$.

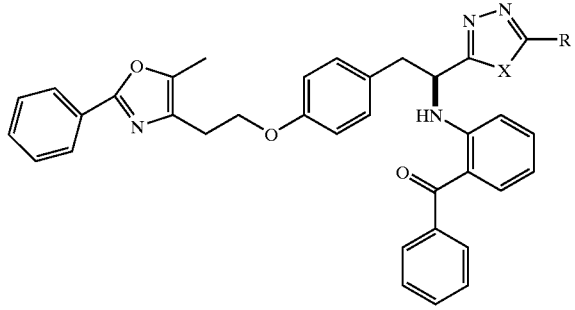

(I)

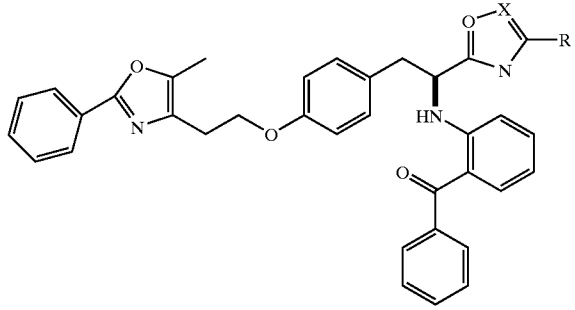

(II)

7 Claims, No Drawings

OXAZOLE PPAR ANTAGONIST

This application is filed pursuant to 35 U.S.C. §371 as a United States National Phase Application of International Application No. PCT/US00/24364 filed Sep. 1, 2000, which claims priority from U.S. Ser. No. 60/152,761 filed Sep. 8, 1999 and 60/199,969 filed Apr. 27, 2000.

The present invention relates to compounds that bind to and affect PPAR-alpha, PPAR-gamma, and PPAR-delta. In another aspect, the present invention relates to methods for prevention or treatment of PPAR-gamma mediated diseases and conditions, and to methods for design of antagonists of PPAR-alpha, PPAR-gamma, and PPAR-delta. In another aspect, the present invention relates to compounds that bind to and affect FXR, LXR-alpha, and LXR-beta. In another aspect, the present invention relates to methods for the prevention or treatment of diseases mediated by FXR, LXR-alpha, and LXR-beta, and to methods for the design of antagonists of FXR, LXR-alpha, and LXR-beta.

Peroxisome Proliferator Activated Receptors (PPARs) are orphan receptors belonging to the steroid/retinoid receptor superfamily of ligand-activated transcription factors. See, for example, Willson, T. M. and Wahli, W., *Curr. Opin. Chem. Biol.*, (1997), Vol. 1, pp 235–241.

Three mammalian PPARs have been identified which are termed PPAR-alpha, PPAR-gamma, and PPAR-delta. PPARs regulate expression of target genes by binding to DNA response elements as heterodimers with the retinoid X receptor. These DNA response elements (PPRE) have been identified in the regulatory regions of a number of genes encoding proteins involved in lipid metabolism and energy balance. The biological role of the PPARs in the regulation of lipid metabolism and storage has been recently reviewed. See, for example, Spiegelman, B. M., *Diabetes*, (1998), Vol. 47, pp 507–514, Schoonjans, K., Martin, G., Staels, B., and Auwerx, J., *Curr. Opin. Lipidol.*, (1997), Vol. 8, pp 159–166, and Brun, R. P., Kim, J. B., Hu, E., and Spiegelman, B. M., *Curr. Opin. Lipidol.*, (1997), Vol. 8, pp 212–218.

PPAR-gamma ligands of the thiazolidinedione class (TZD) enhance the actions of insulin in man and reduce circulating glucose levels in rodent models of diabetes. The PPAR-gamma receptor is expressed in adipose tissue and plays a pivotal role the regulation of adipocyte differentiation in vitro. TZD such as rosiglitazone induce adipocyte differentiation in vitro through activation of the PPAR-gamma receptor. Although there are clearly therapeutic uses for PPAR-gamma ligands in the treatment of diseases of lipid metabolism and energy balance, it is possible that there will be side effects of these drugs. For example, PPAR-gamma ligands that promote adipocyte differentiation in vivo could lead to increased fat accumulation and weight gain. This side effect might offset the beneficial effects of a PPAR-gamma ligand in the treatment of diabetes or other diseases where obesity is a risk factor. See, for example, the Spiegelman and Brun articles cited above.

Essential dietary fatty acids and certain of their eicosanoid metabolites are naturally occurring hormones for the PPAR receptors (Kliewer, 1997; Kliewer 1995). These hormones can promote adipogenesis through activation of the PPAR-gamma receptor. See, for example, Kliewer, S. A., et al., *Proc. Natl. Acad. Sci. USA*, (1997), Vol. 94, pp 4318–4323, and Kliewer, S. A., et al., Cell, (1995), Vol. 83, pp 813–819. Molecules that inhibit the adipogenic effects of endogenous PPAR-gamma hormones may be useful in the treatment of diseases caused by increased fat accumulation or lipid storage. See, for example, Tontonoz, P., Hu, E., and Spiegelman, B. M., *Curr. Opin. Genet. Dev.*, (1995), Vol. 5, pp 571–576. Examples of these diseases are obesity, osteoporosis, and acne. For example, it has also been noted that TZD promote adipogenesis in bone marrow and inhibit expression of markers of the osteoblast phenotype such as alkaline phosphatase. See, for example, Paulik, M. A. and Lenhard, J. M., *Cell Tissue Res.*, (1997), Vol. 290, pp 79–87. These effects may lead to low bone mineral density and osteoporosis. Compounds that promote osteogenesis activity may be useful in the treatment of osteoporosis. Similarly, it is known that the TZDs can promote lipid accumulation in sebocytes. See, for example, Rosenfield, R. L., Deplewski, D., Kentsis, A., and Ciletti, *N. Dermatology*, (1998), Vol. 196, pp 43–46. These effects may lead to sebocyte differentiation and acne formation. Thus, molecules that block adipogenesis in adipocytes, pre-adipocytes, bone marrow, or sebocytes may have beneficial effects in the treatment of obesity, osteoporosis, or acne.

The PPAR-gamma receptor has been found in tissues other than adipose, and it is believed that synthetic PPAR-gamma ligands and natural PPAR-gamma hormones (natural ligands) may have beneficial effects in many other diseases including cardiovascular disease, inflammation, and cancer. See, for example, the Schoonjans article cited above, Ricote, M. et al., *Nature*, (1998), Vol. 391, pp 79–82, and Mueller, E. et al., *Mol. Cell*, (1998), Vol. 1, pp 465–470.

FXR, LXR-alpha, and LXR-beta are orphan receptors belonging to the steroid/retinoid receptor superfamily of ligand-activated transcription factors. See, for example, Repa, Joyce J. and Mangelsdorf, David J., Curr. Opin. Biotechnol. (1999), 10(6), 557–563.

There is precedent among other members of the steroid/retinoid receptor superfamily that synthetic ligands can be identified which mimic many of the beneficial effects but inhibit some of the detrimental side effects of the natural hormones. See, for example, McDonnell, D. P., *Biochem. Soc. Trans.*, (1998), Vol. 26, pp 54–60. These synthetic ligands have been given various labels, including antagonists, anti-hormones, partial agonists, selective receptor modulators, tissue selective ligands, and others. See, for example, Katzenellenbogen, J. A., O'Malley, B. W., and Katzenellenbogen, B. S., *Mol. Endocinol.*, (1996), Vol. 10, pp 119–131.

PPAR-alpha ligands of the fibrate class reduce circulating triglyceride levels and raise HDL. PPAR-alpha ligands may be useful for treatment dyslipidemia and cardiovascular disorders, see Fruchart, J.-C., Duriez, P., and Staels, B., *Curr. Opin. Lipidol.* (1999), Vol. 10, pp 245–257. Less is known about the biology of PPAR-delta ligands, although it has been reported that they raise HDL levels, see Berger, J. et al., *J. Biol. Chem.* (1999), Vol. 274, pp 6718–6725.

Antagonists of PPAR-alpha or PPAR-delta would be useful for characterizing the role of these receptors in mammalian physiology. For example, administration of a PPAR-alpha antagonist or PPAR-delta antagonist to a whole animal would constitute a chemical knock-out of the target receptor. Characterization of the phenotype of this chemical knock-out would indicate the role of the target receptor in mammalian physiology. This knowledge would allow the target receptor to be associated with a particular disease.

Activation of transcription by nuclear receptors involves the recruitment of coactivator proteins. Agonist ligands promote recruitment of coactivator proteins to the receptor by stabilization of the C-terminal AF-2 helix of the ligand binding domain in a conformation that forms a "charge clamp", see Nolte et al, Nature (1998) and Shiau, A. K. et al., Cell (1998), Vol. 95, pp 927–937.

PPAR agonists such as thiazolidinediones, fibrates and fatty acids share a common binding mode to their receptors.

Despite differences in the chemical structure of these agonists, the acidic headgroups of these agonist ligands accept a hydrogen bond from a tyrosine residue in the AF2 helix and/or a histidine or tyrosine residue in helix-5. These hydrogen bonds stabilize the charge clamp. This is a critical step in the activation of the receptor by an agonist ligand, see Xu et al., Mol. Cell (1999), Vol. 3, pp 397–403 and Oberfield et al., PNAS (1999), Vol. 96, pp 6102–6106. In PPAR-alpha these residues are Tyrosine 464 and Tyrosine 314, respectively, using the residue numbering in Genbank S74349 (translation G765240). In PPAR-gamma these residues are Tyrosine 473 and Histidine 323, respectively, using the residue numbering in Genbank X90563 (translation G1490313). In PPAR-delta these residues are Tyrosine 437 and Histidine 287, respectively, using the residue numbering in Genbank L07592 (translation G190230).

Structural studies suggest that many nuclear receptors share a similar general mechanism of activation, where binding of ligand stabilizes the AF2 helix, thereby stabilizing the charge clamp and allowing coactivators to bind. X-ray structures of the estrogen receptor, progesterone receptor, thyroid receptor, retinoic acid receptor and vitamin D receptor show that, in these cases, the ligand generally makes lipophilic contacts with the AF2 helix. In some cases, such as the estrogen receptor, these contacts are very tenuous.

The PPARs are unusual in having a tyrosine residue in the AF2 helix available to make a direct hydrogen bond with the ligand. The interaction with this tyrosine appears to be essential for full activation of the PPAR. Sequence analysis and homology modeling indicate that FXR, LXR-alpha, and LXR-beta are similar to the PPARs in having an amino acid in the AF2 helix which can form a hydrogen bond with the ligand. In human FXR, this residue is Tryptophan 469, using the residue numbering in Genbank U68233 (translation G1546084). In human LXR-alpha, this residue is Tryptophan 443, using the residue number in Genbank U22662 (translation G726513). In human LXR-beta, this residue is Tryptophan 457, using the residue numbering in Genbank U07132 (translation G641962). Homology modeling further suggests that the ligand can make a hydrogen bond with the side chain NH of this AF2 tryptophan, and that this hydrogen bond may be essential for full activation of FXR, LXR-alpha, and LXR-beta.

As used herein, a "PPAR-gamma ligand" is a compound that binds to human PPAR-gamma with a pKi of greater than 5 when tested in the binding assay described below. As used herein a "PPAR-gamma antagonist" is a PPAR-gamma ligand that gives greater than 50% inhibition of lipogenesis when tested in the adipocyte differentiation assay described below and greater than 50% inhibition of transactivation by 100 nM rosiglitazone when tested in the cell-based reporter assay described below.

As used herein, a "PPAR-alpha ligand" is a compound that binds to human PPAR-alpha with a pKi of greater than 5 when tested in the binding assay described below. As used herein a "PPAR-alpha antagonist" is a PPAR-alpha ligand that gives greater than 50% inhibition of transactivation by 100 nM 2-(4-(2-(1-Heptyl-3-(4-fluorophenyl)ureido)ethyl) phenoxy)-2-methylpropionic acid when tested in the cell-based reporter assay described below.

As used herein, a "PPAR-delta ligand" is a compound that binds to human PPAR-alpha with a pKi of greater than 5 when tested in the binding assay described below. As used herein a "PPAR-delta antagonist" is a PPAR-delta ligand that gives greater than 50% inhibition of transactivation by 1000 nM 2-(4-(2-(1-Heptyl-3-(4-fluorophenyl)ureido)ethyl) phenoxy)-2-methylpropionic acid when tested in the cell-based reporter assay described below.

As used herein, a "PPAR antagonist" is a compound that is an antagonist of any one, or more than one, PPAR. As used herein, a "PPAR agonist" is a compound that is an agonist of any one, or more than one, PPAR.

As used herein, an "FXR ligand" is a compound that binds to human FXR with a pKi of greater than 5 when tested in an FXR binding assay. As used herein, an "FXR antagonist" is an FXR ligand that gives greater than 50% inhibition of transactivation when tested in an FXR cell-based reporter assay such as that described by Parks, D. J., et al., Science (1999) Vol. 284, pp 1365–1368.

As used herein, an "LXR-alpha ligand" is a compound that binds to human LXR-alpha with a pKi of greater than 5 when tested in an LXR-alpha binding assay such as that described in Janowski, B. A., et al., Proceedings of the National Academy of Sciences (USA) (1999) Vol. 96, pp. 266–271. As used herein, an "LXR-alpha antagonist" is an LXR-alpha ligand that gives greater than 50% inhibition of transactivation when tested in an LXR-alpha cell-based reporter assay such as that described by Janowski, B. A., et al., Proceedings of the National Academy of Sciences (USA) (1999) Vol. 96, pp. 266–271.

As used herein, an "LXR-beta ligand" is a compound that binds to human LXR-beta with a pKi of greater than 5 when tested in an LXR-beta binding assay such as that described in Janowski, B. A., et al., Proceedings of the National Academy of Sciences (USA) (1999) Vol. 96, pp. 266–271. As used herein, an "LXR-beta antagonist" is an LXR-beta ligand that gives greater than 50% inhibition of transactivation when tested in an LXR-beta cell-based reporter assay such as that described by Janowski, B. A., et al., Proceedings of the National Academy of Sciences (USA) (1999) Vol. 96, pp. 266–271.

Briefly, in one aspect, the present invention discloses compounds of Formula (I) or (II), or pharmaceutically acceptable salts or solvates thereof,

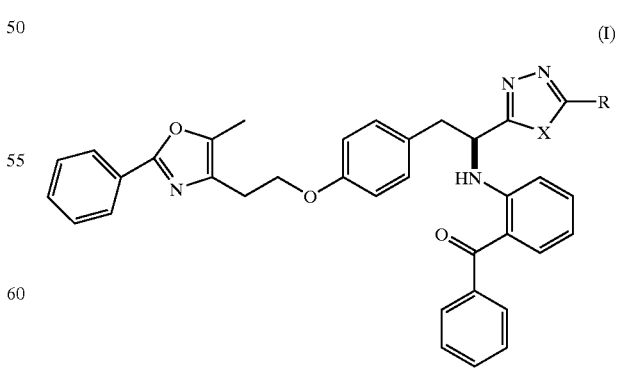

(I)

where in Formula (I) X is O, S, or NH;

and R is methyl, ethyl, n-propyl, i-propyl, cyclopropyl, n-butyl, phenyl, or —$CH_2OCH_3$,

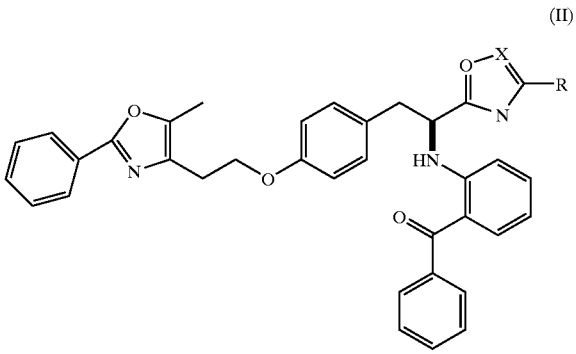
(II)

where in Formula (II) X is C or N;
and R is methyl, ethyl, n-propyl, i-propyl, —CH$_2$OCH$_3$, or —CO$_2$CH$_3$. These compounds are PPAR gamma antagonists and are close analogues of PPAR gamma agonists.

In another aspect, the present invention discloses a method for prevention or treatment of a PPAR-gamma mediated disease or condition comprising administration of a therapeutically effective amount of a compound of this invention. As used herein, "a compound of the invention" means a compound of formula (I) or (II) or a pharmaceutically acceptable salt, or solvate thereof.

In another aspect, the present invention discloses a method for preparation of, or design of, PPAR antagonists comprising chemical modification of a PPAR agonist or ligand to a) prevent formation of a hydrogen bond between the agonist and tyrosine or histidine involved in receptor activation, and/or to b) displace the tyrosine or histidine involved in receptor activation from their agonist bound position, wherein little or no additional modification or changes in the structure of the agonist are made. The resulting compounds are PPAR antagonists that are close structural analogues of the corresponding PPAR agonist.

In another aspect, the present invention provides PPAR antagonists prepared using the method of this invention. As used herein, an "antagonist of this invention" means a PPAR antagonist, or a pharmaceutically acceptable salt, or solvate thereof, that was prepared or designed using the method of this invention.

In another aspect, the present invention provides a method for prevention or treatment of a PPAR mediated disease or condition comprising administration of a therapeutically effective amount of a PPAR antagonist of this invention.

In another aspect, the present invention discloses a method for preparation of, or design of, FXR antagonists comprising chemical modification of an FXR agonist or ligand, to a) prevent formation of a hydrogen bond between the agonist and the tryptophan residue involved in receptor activation, and/or to b) displace the tryptophan residue from its agonist bound position, wherein little or no additional modification or changes in the structure of the agonist are made. The resulting compounds are FXR antagonists that are close structural analogues of the corresponding FXR agonist.

In another aspect, the present invention provides a method for prevention or treatment of a FXR mediated disease or condition comprising administration of a therapeutically effective amount of a FXR antagonist of this invention.

In another aspect, the present invention discloses a method for preparation of, or design of, LXR-alpha antagonists comprising chemical modification of an LXR-alpha agonist or ligand, to a) prevent formation of a hydrogen bond between the agonist and where the tryptophan residue in the AF2 helix that stabilizes the charge clamp, and/or to b), wherein little or no additional modification or changes in the structure of the agonist are made. The resulting compounds are LXR-alpha antagonists that are close structural analogues of the corresponding LXR-alpha agonist.

In another aspect, the present invention provides a method for prevention or treatment of an LXR-alpha mediated disease or condition comprising administration of a therapeutically effective amount of an LXR-alpha antagonist of this invention.

In another aspect, the present invention discloses a method for preparation of, or design of, LXR-beta antagonists comprising chemical modification of an LXR-beta agonist or ligand, to a) prevent formation of a hydrogen bond between the agonist and where the tryptophan residue in the AF2 helix that stabilizes the charge clamp, and/or to b), wherein little or no additional modification or changes in the structure of the agonist are made. The resulting compounds are LXR-beta antagonists that are close structural analogues of the corresponding LXR-beta agonist.

In another aspect, the present invention provides a method for prevention or treatment of an LXR-beta mediated disease or condition comprising administration of a therapeutically effective amount of an LXR-beta antagonist of this invention.

Suitable compounds of the present invention include:
  (S)-{{2-[1-(2-Benzoylphenyl)amino]-2-{4-[2-(5-methyl-2-phenyloxazol-4-yl)ethoxy]phenyl}ethyl}}-5-propyl-1,3,4-oxadiazole,
  (S)-{{2-[1-(2-Benzoylphenyl)amino]-2-{4-[2-(5-methyl-2-phenyloxazol4-yl)ethoxy]phenyl}ethyl}}-5-ethyl-1,3,4-oxadiazole,
  (S)-{{2-[1-(2-Benzoylphenyl)amino]-2-{4-[2-(5-methyl-2-phenyloxazol-4-yl)ethoxy]phenyl}ethyl}}-5-phenyl-1,3,4-oxadiazole,
  (S)-{{2-[1-(2-Benzoylphenyl)amino]-2-{4-[2-(5-methyl-2-phenyloxazol-4-yl)ethoxy]phenyl}ethyl-5-butyl-1,3,4-oxadiazole,
  (S)-{{2-[1-(2-Benzoylphenyl)amino]-2-{4-[2-(5-methyl-2-phenyloxazol-4-yl)ethoxy]phenyl}ethyl}}-5-methyl-1,3,4-oxadiazole,
  (S)-{{2-[1-(2-Benzoylphenyl)amino]-2-{4-[2-(5-methyl-2-phenyloxazol-4-yl)ethoxy]phenyl}ethyl}}-5-methoxymethyl-1,3,4-oxadiazole,
  (S)-{{2-[1-(2-Benzoylphenyl)amino]-2-{4-[2-(5-methyl-2-phenyloxazol-4-yl)ethoxy]phenyl}ethyl}}-5-cyclopropyl-1,3,4-oxadiazole,
  (S)-{{5-[1-(2-Benzoylphenyl)amino]-2-{4-[2-(5-methyl-2-phenyloxazol-4-yl)ethoxy]phenyl}ethyl}}-3-methyl-1,2,4-oxadiazole,
  (S)-{{5-[1-(2-Benzoylphenyl)amino]-2-{4-[2-(5-methyl-2-phenyloxazol-4-yl)ethoxy]phenyl}ethyl}}-3-propyl-1,2,4-oxadiazole,
  (S)-{{5-[1-(2-Benzoylphenyl)amino]-2-{4-[2-(5-methyl-2-phenyloxazol-4-yl)ethoxy]phenyl}ethyl}}-3-methoxymethyl-1,2,4-oxadiazole,
  (S)-{{5-[1-(2-Benzoylphenyl)amino]-2-{4-[2-(5-methyl-2-phenyloxazol-4-yl)ethoxy]phenyl}ethyl}}-3-ethyl-1,2,4-oxadiazole,
  (S)-{{2-[1-(2-Benzoylphenyl)amino]-2-{4-[2-(5-methyl-2-phenyloxazol-4-yl)ethoxy]phenyl}ethyl}}-5-isopropyl-1,3,4-thiadiazole,
  (S)-{{2-[1-(2-Benzoylphenyl)amino]-2-{4-[2-(5-methyl-2-phenyloxazol-4-yl)ethoxy]phenyl}ethyl}}-5-propyl-1,3,4-thiadiazole, (S){{2-[1-(2-Benzoylphenyl)amino]-2-{4-[2-(5-methyl-2-phenyloxazol-4-yl)ethoxy]phenyl}ethyl}}-5-methyl-1,3,4-thiadiazole, (S)-{{2-[1-(2-Benzoylphenyl)amino]-2-{4-[2-(5-methyl-2-phenyloxazol-4-yl)ethoxy]phenyl}ethyl}}-5-methyl-1,3,4-triazole, (S)-{{2-[1-(2-Benzoylphenyl)amino]-2-{4-[2-(5-methyl-2-phenyloxazol-4-yl)ethoxy]phenyl}ethyl}}-5-propyl-1,3,4-triazole, (S)-{{2-[1-(2-Benzoylphenyl)amino]-2-{4-[2-(5-methyl-2-phenyloxazol-4-yl)ethoxy]phenyl}ethyl}}-4-ethyl-1,3-oxazole, (S)-{{2-[1-(2-Benzoylphenyl)amino]-244-[2-(5-methyl-2-phenyloxazol-4-yl)ethoxy]phenyl}ethyl}}-4-isopropyl-1,3-oxazole, (S)-{{2-[1-(2-Benzoylphenyl)amino]-2-{4-[2-(5-methyl-2-phenyloxazol-4-yl)ethoxy]phenyl}ethyl}}-4-propyl-1,3-oxazole, (S)-{{2-[1-(2-Benzoylphenyl)amino]-2-{4-[2-(5-methyl-2-phenyloxazol-4-yl)ethoxy]phenyl}ethyl}}-4-methoxycarbonyl-1,3-oxazole, and pharmaceutically acceptable salts and solvates thereof.

Preferred compounds of the present invention include:

(S)-{{2-[1-(2-Benzoylphenyl)amino]-2-{4-[2-(5-methyl-2-phenyloxazol-4-yl)ethoxy]phenyl}ethyl}}-5-propyl-1,3,4-oxadiazole and pharmaceutically acceptable salts and solvates thereof.

The present invention discloses a method for preparing a PPAR antagonist through chemical modification of a PPAR agonist or ligand, where the PPAR agonist or ligand possesses a functional group that accepts a hydrogen bond from tyrosine residues and/or histidine residues within the ligand binding domain that stabilize the charge clamp. Suitable chemical modifications replace the hydrogen bond accepting functional group with a non-hydrogen bond accepting functional group. Preferably a non-hydrogen bond accepting functional group has a pKa greater than 7. Preferably the chemical modifications do not change the binding position or orientation of the ligand within the ligand binding domain, but do alter the side-chain orientation of the tyrosine residues and/or histidine residues within the ligand binding domain that stabilize the charge clamp.

Specifically, for PPAR agonists or ligands where a carboxylic acid accepts a hydrogen bond from tyrosine residues and/or histidine residues within the ligand binding domain that stabilize the charge clamp, the carboxylic acid can be replaced with a 5-membered heterocyclic group including 1,3,4-oxadiazole, 1,2,4-oxadiazole, 1,3,4-thiadiazole, 1,3,4-triazole or 1,3-oxazole. Other suitable 5-membered heterocyclic groups include 1,2,3-oxadiazole, 1,2,5-oxadiazole, 1,2,3-thiadiazole, 1,2,4-thiadiazole, 1,2,5-thiadiazole, furan, thiophene, pyrrole, pyrazole, imidizole, isoxazole, isothiazole, N-substituted tetrazoles and other 5-membered heterocyclic groups containing one or more heteroatoms selected from nitrogen, oxygen and sulfur. The 5-membered heterocyclic group may be optionally substituted with 1 or 2 groups of 1 to 10 heavy atoms selected from carbon, nitrogen, oxygen and sulfur. When the heavy atom is carbon it can be optionally substituted with 1 to 3 fluorines. Furthermore, a carboxylic acid group can be replaced with a phenyl ring or a 6-membered heterocyclic group including pyridine, pyrazine, pyridazine, pyrimidine, triazine, tetrazine and other 6-membered heterocyclic rings containing one or more heteroatoms. The phenyl or 6-membered heterocyclic group can be optionally substituted with one to three groups of 1 to 10 heavy atoms selected from carbon, nitrogen, oxygen and sulfur. When the heavy atom is carbon it can be optionally substituted with 1 to 3 fluorines.

Specifically, for PPAR agonists or ligands where the free N-H of a thiazolidinedione or oxazolidinedione accepts a hydrogen bond from a tyrosine residue within the ligand binding domain that stabilizes the charge clamp, the thiazolidinedione or oxazolidinedione can be replaced with one of the heterocyclic groups listed above. Alternatively, a thiazolidinedione or oxazolidinedione may be N-substituted with a group consisting of 1 to 10 heavy atoms selected from C, N, O and S. When the heavy atom is carbon it can be optionally substituted with 1 to 3 fluorines. Furthermore, a thiazolidinedione or oxazolidinedione can be replaced with a hydantoin optionally substituted on nitrogen with one or two groups consisting of 1 to 10 heavy atoms selected from carbon, nitrogen, oxygen and sulfur. When the heavy atom is carbon it can be additionally substituted with 1 to 3 fluorines.

The present invention discloses a method for preparing an FXR antagonist through chemical modification of an FXR agonist or ligand, where the FXR agonist or ligand possesses a functional group that accepts a hydrogen bond from the tryptophan residue in the AF2 helix that stabilizes the charge clamp. This is tryptophan 469 in the human FXR. Suitable chemical modifications replace the hydrogen bond accepting functional group with a functional group that cannot accept the hydrogen bond. Preferably the chemical modifications do not substantially change the binding position or orientation of the ligand within the ligand binding domain, but do alter the conformation of the tryptophan side-chain, or displace the AF2 helix, or otherwise permit the AF2 helix to move out of the active position, thereby destabilizing the charge clamp.

The present invention discloses a method for preparing an LXR-alpha antagonist through chemical modification of an LXR-alpha agonist or ligand, where the LXR-alpha agonist or ligand possesses a functional group that accepts a hydrogen bond from the tryptophan residue in the AF2 helix that stabilizes the charge clamp. This is tryptophan 443 in the human LXR-alpha. Suitable chemical modifications replace the hydrogen bond accepting functional group with a functional group that cannot accept the hydrogen bond. Preferably the chemical modifications do not substantially change the binding position or orientation of the ligand within the ligand binding domain, but do alter the conformation of the tryptophan side-chain, or displace the AF2 helix, or otherwise permit the AF2 helix to move out of the active position, thereby destabilizing the charge clamp.

The present invention discloses a method for preparing an LXR-beta antagonist through chemical modification of an LXR-beta agonist or ligand, where the LXR-beta agonist or ligand possesses a functional group that accepts a hydrogen bond from the tryptophan residue in the AF2 helix that stabilizes the charge clamp. This is tryptophan 457 in the human LXR-beta. Suitable chemical modifications replace the hydrogen bond accepting functional group with a functional group that cannot accept the hydrogen bond. Preferably the chemical modifications do not substantially change the binding position or orientation of the ligand within the ligand binding domain, but do alter the conformation of the tryptophan side-chain, or displace the AF2 helix, or otherwise permit the AF2 helix to move out of the active position, thereby destabilizing the charge clamp.

Specifically, for FXR, LXR-alpha, and/or LXR-beta agonists or ligands where a hydroxyl group accepts a hydrogen bond from the AF2 tryptophan residue, the hydroxyl group can be removed, moved to the position corresponding to the opposite chirality, or replaced by a methyl group, amine, or other group that fails to accept hydrogen bonds. For FXR, LXR-alpha, and/or LXR-beta agonists or ligands where an ether oxygen accepts a hydrogen bond from the AF2 tryptophan residue, the ether oxygen can be removed, or replaced by a sulfur, methylene group or other group that fails to accept hydrogen bonds. For FXR, LXR-alpha, and/or LXR-beta agonists or ligands where a carbonyl oxygen accepts a hydrogen bond from the AF2 tryptophan residue, the carbonyl oxygen can be removed, or replaced by a carbon, nitrogen, sulfur or other group that fails to accept a hydrogen bond from the AF2 tryptophan residue. For FXR, LXR-alpha, and/or LXR-beta agonists or ligands where a carboxyl group accepts a hydrogen bond from the AF2 tryptophan residue, the carboxyl group can be removed, or replaced by a 5-membered heterocyclic group, which may optionally be substituted with 1 or 2 groups of 1 to 10 heavy atoms selected from carbon, nitrogen, oxygen or sulfur. Alternatively, the carboxyl group can be replaced by a phenyl ring or six-membered heterocyclic group, or other group that fails to accept hydrogen bonds. This chemical modification will usually reduce the activation of transcription by FXR, LXR-alpha, and/or LXR-beta, and may sometimes reduce the binding affinity. If the activation of transcription is substantially reduced and the binding affinity is sufficient, then the modified compound may serve as a useful antagonist for FXR, LXR-alpha, and/or LXR-beta.

It will be appreciated by those skilled in the art that the compounds or antagonists of the present invention may be utilised in the form of a pharmaceutically acceptable salt or solvate thereof. Physiologically acceptable salts include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

It will be appreciated by those skilled in the art that reference herein to treatment extends to prophylaxis as well as the treatment of established diseases or symptoms. Moreover, it will be appreciated that the amount of a compound or antagonist of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day.

While it is possible that compounds or antagonists of the present invention may be therapeutically administered as the raw chemical, it is preferable to present the active ingredient as part of a pharmaceutical formulation.

Formulations of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. The tablets may be coated according to methods well known in the art.

Alternatively, the compounds and antagonists of the present invention may be incorporated into oral liquid preparations such as aqueous or oily suspensions, solutions, emulsions, syrups or elixirs, for example. Moreover, formulations containing these compounds or antagonists may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds and antagonists of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

The compounds and antagonists of this invention can be prepared by standard organic chemistry as illustrated by the accompanying working examples. The following examples are set forth to illustrate the synthesis of some particular compounds of the present invention and to exemplify general processes. Accordingly, the following Examples section is in no way intended to limit the scope of the invention contemplated herein.

EXAMPLES

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); µL (microliters); N (normal); mM (millimolar); mmol (millimoles); i. v. (intravenous); Hz (Hertz); MHz (megahertz); mol (moles); RT or rt (room temperature); min (minutes); h (hours); mp. (melting point); TLC (thin layer chromatography); HPLC (high pressure liquid chromatography); ms (mass spectrum); ES+ (electrospray); $R_f$ (retention fraction); ($t_r$ (retention time); RP (reverse phase); MeOH (methanol); TFA (trifluoroacetic acid); HCl (hydrochloric acid); $HCO_2H$ (formic acid); THF (tetrahydrofuran); $CH_3CN$ (acetonitrile); EtOH (ethanol); $CDCl_3$ (deuterated chloroform); DMSO (dimethylsulfoxide); DMSO-$d_6$ (dimethylsulfoxide-deuterated); EtOAc (ethyl acetate); DCM or $CH_2Cl_2$ (dichloromethane); DMF (dimethylformamide); $Et_3N$ (triethylamine); $MgSO_4$ (magnesium sulfate); $H_2O$ (water); LAH (lithium aluminum hydride; NaH (sodium hydride); $Na_2CO_3$ (sodium carbonate); $Na_2SO_4$ (sodium sulfate); $MnO_2$ (manganese dioxide); NaOH (sodium hydroxide; LiOH (lithium hydroxide); DIEA (diisopropylethylamine); $Et_2O$ (diethyl ether; diethyl azodicaboxylate (DEAD); tert-butyloxycarbonyl (BOC); $NaHCO_3$ (saturated aqueous sodium bicarbonate). Brine refers to a saturated aqueous solution of NaCl. Unless otherwise indicated, all temperatures are expressed in ° C. (degrees Centigrade). All reactions conducted at room temperature unless otherwise noted.

The $^1$H NMR spectra were recorded on a Varian VXR-300, a Varian Unity-300, or a Varian Unity-400 instrument. Chemical shifts are expressed in parts per million (ppm, θ units). Coupling constants are in units of hertz (Hz). Splitting patterns are designated as s, singlet; d, doublet; t, triplet; q, quartet; m, multiplet; br, broad; hept, heptuplet.

Low-resolution mass spectra (MS) were recorded on a JOEL JMS-AX505HA, JOEL SX-102 or a SCIEX-APiiii spectrometers. All mass spectra were taken under electrospray ionization (ES, either in the positive ion mode or negative ion mode) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, iodine staining, or 7% ethanolic phosphomolybdic acid or p-anisldehyde solutions. Flash column chromatography was performed on silica gel (230–400 mesh, Merck).

Analytical purity was assessed on a Hewlett Packard series 1050 or 1100 system equipped with a diode array spectrometer. The stationary phase was either a Dynamax C8 column (25 cm×4.1 mm), a Dynamax 60A C18 column (25 cm×4.6 mm), a Vydac C18 column (5 m, 4.6 mm×250 mm), a Supelco C18 column (m, 4.6 mm×150 mm), or a Rainin C18 column (5 m, 4.6 mm×250 mm). The flow rate was 1.0 to 1.5 ml/min. (t0=2.8 or 3.0 min.) and the solvent systems were as described below. Enantiomeric purity was assessed using either a Chiralpak AD column (25 cm×4.6 mm) or a Chiralpak OD column (25 cm×4.6 mm) on either a Hewlet Packard series 1050 HPLC system equipped with a diode array spectrometer or on a Supercritical Fluid (SFC) system using $CO_2$/methanol as the mobile phase.

The following working examples are all compounds of this invention. These compounds were designed and prepared using the design and preparation method of this invention. Therefore, the following working Examples are illustrative of the compounds of this invention, the antagonists of this invention, and the method of design or preparation of this invention.

Method of Design

Compounds were designed to replace the acidic group of a PPAR-gamma agonist by an arrangement of atoms that were a) no longer capable of forming a strong hydrogen bond with tyrosine 473 or histidine 323 of the ligand binding domain, and/or b) displaced tyrosine 473 or histidine 323 of the ligand binding domain from their agonist-bound positions. Compound 20 described in Henke, B. R. et al., *J. Med. Chem.*, (1998), Vol. 41, 5020–5036, is a PPAR gamma agonist and contains a carboxylic acid group that is capable of forming a hydrogen bond with tyrosine 473 and/or histidine 323 of the PPAR gamma ligand binding domain. In the following examples, the acid group was replaced by other groups and no other modifications were made to the structure of Compound 20.

Example 1

(S)-{{2-[1-(2-Benzoylphenyl)amino]-2-{4-[2-(5-methyl-2-phenyloxazol-4-yl)ethoxy]phenyl}ethyl}}-5-propyl-1,3,4-oxadiazole (S)-{{2-[1-(2-Benzoylphenyl)amino]-2-{4-[2-(5-methyl-2-phenyloxazol-4-yl)ethoxy]phenyl}ethyl}}-5-propyl-1,3,4-oxadiazole was designed as a PPAR-gamma antagonists by replacement of the carboxylic acid in compound 20 with a substituted 5-membered ring heterocycle.

To a stirred, cooled (0° C.) solution of (2S)-[(2-benzoylphenyl)amino]-3-{4-[2-(5-methyl-2-phenyloxazol-4-yl)ethoxy]phenyl}propionic acid [compound 20 described in Henke, B. R. et al., *J. Med. Chem.*, (1998), Vol. 41, 5020–5036] (5.00 g, 9.15 mmol) in THF (120 mL) was added 4-methylmorpholine (1.20g, 11.8 mmol) followed by isobutyl chloroformate (1.79 g, 13.1 mmol). The resulting suspension was stirred for 30 min and then filtered into a stirred, cooled (0° C.) solution of hydrazine (1.43 g, 44.6 mmol) in THF (80 mL). After stirring for 45 min, the mixture was poured into EtOAc and washed with water, saturated aqueous ammonium chloride, brine and dried over $MgSO_4$. Removal of solvent under reduced pressure provided the desired monoacyl hydrazide (5.35 g) as a yellow solid.

To a stirred solution of the above monoacyl hydrazide (5.34 g) and trimethyl orthobutyrate (4.07 g, 27.5 mmol) in dioxane (100 mL) was added methanesulfonic acid (178 mg, 1.85 mmol). The mixture was placed in an oil bath preheated to 105° C. and stirred for 15 min. After cooling to room temperature, the mixture was poured into EtOAc, washed with saturated aqueous $NaHCO_3$, brine and dried over $MgSO_4$. Solvent was removed under reduced pressure giving a yellow oil. This material was combined with three other batches prepared in a similar manner from the above referenced carboxylic acid (5.54 g, 5.99 g, and 5.06 g) and chromatographed on silica gel eluting with 2:3 EtOAc in hexane to afford 20.8 g of a sticky yellow glass. This material was dissolved in $Et_2O$, allowed to evaporate slowly and dried in vacuo to afford the desired 1,3,4-oxadiazole (19.7 g, 84%) as an amorphous yellow solid. Mp=78–82° C.; 300 MHz $^1$H NMR ($CDCl_3$) δ 8.97 (d, 1H), 7.97 (m, 2H), 7.59–7.30 (m, 10H), 7.12 (d, 2H), 6.86 (d, 1H), 6.79 (d, 2H), 6.59 (t, 1H), 5.09 (m, 1H), 4.18 (t, 2H), 3.30 (d, 2H), 2.94

(t, 2H), 2.75 (t, 2H), 2.34 (s, 3H), 1.73 (m, 2H), 0.95 (t, 3H); Low resolution MS (ES+) m/e 613 (MH+); Anal. Calc'd. for $C_{38}H_{36}N_4O_4 \cdot 0.5\ H_2O$: C, 73.41; H, 6.00; N, 9.01. Found: C, 73.51; H, 6.04; N, 9.01.

Example 2

(S)-{{2-[1-(2-Benzoylphenyl)amino]-2-{4-[2-(5-methyl-2-4-yl)ethoxy]phenyl}ethyl}}-5-ethyl-1,3,4-oxadiazole Prepared from the intermediate (2S)-[(2-benzoylphenyl)amino]-3-{4-[2-(5-methyl-2-phenyloxazol-4-yl)ethoxy]phenyl{propionic hydrazide described in Example 1 and triethylorthopropionate to provide the desired 1,3,4-oxadiazole (82%) as a yellow foam. Low resolution MS (ES+) m/e 599 (MH+); 400 MHz $^1$H NMR (CDCl$_3$) δ 8.97 (d, 1H), 7.97 (m, 2H), 7.59–7.31 (m, 10H), 7.13 (d, 2H), 6.8 (d, 1H), 6.80 (d, 2H), 6.59 (t, 1H), 5.09 (m, 1H), 4.18 (t, 2H), 3.30 (d, 2H), 2.94 (t, 2H), 2.81 (m, 2H), 2.34 (s, 3H), 1.31 (t, 3H); Anal. Calc'd. for $C_{37}H_{34}N_4O_4 \cdot 0.5\ H_2O$: C, 73.13; H, 5.81; N, 9.22. Found: C, 73.06; H, 5.74; N, 8.82.

Example 3

(S )-{{2-[1-(2-Benzoylphenyl)amino]-2-{4-[2-(5-methyl-2-phenyloxazol-4-yl)ethoxy]phenyl}ethyl}}-5-phenyl-1,3,4-oxadiazole Prepared from the intermediate (2S)-[(2-benzoylphenyl)amino]-3-{4-[2-(5-methyl-2-phenyloxazol4-yl )ethoxy]phenyl}propionic hydrazide described in Example 1 and trimethyl orthobenzoate to provide the desired 1,3,4-oxadiazole (85%) as a yellow foam. Low resolution MS (ES+) m/e 647 (MH+); 300 MHz $^1$H NMR (CDCl$_3$) δ 9.05 (d, 1H), 7.98 (m, 4H), 7.61–7.31 (m, 13H), 7.19 (d, 2H), 6.94 (d, 1H), 6.81 (d, 2H), 6.60 (t, 1H), 5.19 (m, 1H), 4.17 (t, 2H), 3.38 (d, 2H), 2.94 (t, 2H), 2.34 (s, 3H).

Example 4

(S)-{{2-[1-(2-Benzoylphenyl)amino]-2-{4-[2-(5-methyl-2-phenyloxazol-4-yl)ethoxy]phenyl}ethyl}}-5-butyl-1,3,4-oxadiazole To a stirred solution of (2S)-[(2-benzoylphenyl)amino]-3-4-[2-(5-methyl-2-phenyloxazol-4-yl)ethoxylphenyl}propionic acid referenced in Example 1 (200 mg, 0.37 mmol) in CH$_2$Cl$_2$ (4 mL) was added 1-hydroxybenzotriazole (56 mg, 0.41 mmol) and 1-(3-dimethylaminopropyl)-3-ethylcarbodiimide hydrochloride (773 mg, 0.40 mmol) followed by 4-methylmorpholine (92 mg, 0.91 mmol). The mixture was stirred for 5 minutes and then valeric hydrazide (50 mg, 0.43 mmol) was added. After stirring overnight, the resulting thick suspension was filtered and the collected solid was washed with CH$_2$Cl$_2$ and dried in vacuo to afford the desired diacyl hydrazide (157 mg, 66%) as a yellow solid.

A suspension of P$_2$O$_5$ (137 mg, 0.97 mmol) in methanesulfonic acid (1.04 g, 10.8 mmol) was stirred for 1 hr. To this mixture was added the above diacyl hydrazide (121 mg, 0.19 mmol) and the resulting mixture was placed in an oil bath preheated to 75° C. The mixture slowly became homogeneous and was left overnight. After cooling to room temperature, the mixture was diluted with CH$_2$Cl$_2$ and carefully added to a stirring solution of 2M aqueous K$_2$CO$_3$. The two layers were separated and the aqueous layer was further extracted with CH$_2$Cl$_2$. The combined organic layers were washed with brine, dried over MgSO$_4$ and evaporated to dryness under reduced pressure. The remaining residue was chromatographed on silica gel eluting with 1:3 EtOAc in hexane to provide the desired 1,3,4-oxadiazole (68 mg, 57%) as a yellow foam. Low resolution MS (ES+) m/e 627 (MH+); 400 MHz $^1$H NMR (CDCl$_3$) δ 8.97 (d, 1H), 7.97 (m, 2H), 7.59–7.30 (m, 10H), 7.12 (d, 2H), 6.86 (d, 1H), 6.79 (d, 2H), 6.60 (t, 1H), 5.09 (m, 1H), 4.18 (t, 2H), 3.30 (d, 2H), 2.94 (t, 2H), 2.77 (m, 2H), 2.36 (s, 3H), 1.68 (m, 2H), 1.33 (m, 2H). 0.88 (t, 3H); Anal. Calc'd. for $C_{39}H_{38}N_4O_4 \cdot 0.25\ H_2O$: C, 74.21; H, 6.15; N, 8.88. Found: C, 74.20; H, 6.39; N, 8.48.

Example 5

(S)-{{2-[1-(2-Benzoylphenyl)amino]-2-{4-[2-(5-methyl-2-phenyloxazol-4-yl)ethoxy]phenyl}ethyl}}-5-methyl-1,3,4-oxadiazole Prepared by the method described in Example 4 from (2S)-[(2-benzoylphenyl)amino]-3-{4-[2-(5-methyl-2-phenyloxazol-4-yl)ethoxy]phenyl}propionic acid referenced in Example 1 and acetyl hydrazide. Cyclization provided the desired 1,3,4-oxadiazole (52%) as a yellow foam. Low resolution MS (ES+) m/e 585 (MH+); 400 MHz $^1$H NMR (CDCl$_3$) δ 8.98 (d, 1H), 7.96 (m, 2H), 7.59–7.30 (m, 10H), 7.14 (d, 2H), 6.86 (d, 1H), 6.80 (d, 2H), 6.61 (t, 1H), 5.08 (m, 1H), 4.18 (t, 2H), 3.29 (d, 2H), 2.94 (t, 2H), 2.50 (s, 3H), 2.35 (s, 3H).

Example 6

(S)-{{2-[1-(2-Benzoylphenyl)amino]-2-{4-[2-(5-methyl-2-phenyloxazol-4-yl)ethoxy]phenyl}ethyl}}-5-methoxymethyl-1,3,4-oxadiazole To a stirred solution of the intermediate (2S)-[(2-benzoylphenyl)amino]-3-{4-[2-(5-methyl-2-phenyloxazol-4-yl)ethoxy]phenyl}propionic hydrazide described in Example 1 (242 mg, 0.43 mmol) in CH$_2$Cl$_2$ (5 mL) was added triethylamine (109 mg, 1.08 mmol) followed by methoxyacetyl chloride (53 mg, 0.49 mmol). After stirring overnight, the mixture was diluted with CH$_2$Cl$_2$, washed with 1N aqueous HCl, brine and dried over MgSO$_4$. Solvent was removed under reduced pressure. The remaining residue was chromatographed on silica gel eluting with 1:1 EtOAc in hexane followed by EtOAc to afford the desired diacyl hydrazide (161 mg, 59%) as a yellow solid.

The above diacyl hydrazide (130 mg, 0.21 mmol) was placed in a reuseable thick walled pressure tube and suspended in chlorobenzene (0.3 mL) with stirring. Hexamethyldisilazane (230 mg, 1.42 mmol) and 1 M tetrabutylammonium fluoride in THF (15 µL, 0.015 mmol) was added to the suspension. The reaction vessel was sealed and placed in an oil bath preheated to 130° C. After 72 hr, the mixture was cooled to room temperature, transferred to a column of silica gel and eluted with 1:9 EtOAc in hexane followed by 3:7 EtOAc in hexane and 1:1 EtOAc in hexane. Further purification on silica gel using radial chromatography provided the desired 1,2,4-oxadiazole (19 mg, 14%) as a yellow foam. Low resolution MS (ES+) m/e 615 (MH+); 400 MHz $^1$H NMR (CDCl$_3$) δ 9.00 (d, 1H), 7.99 (m, 2H), 7.59–7.30 (m, 10H), 7.13 (d, 2H), 6.85 (d, 1H), 6.79 (d, 2H), 6.60 (t, 1H), 5.12 (m, 1H), 4.58 (s, 2H), 4.19 (t, 2H), 3.38 (s, 3H), 3.33 (d, 2H), 2.96 (t, 2H), 2.38 (s, 3H).

Example 7

(S)-{{2-[1-(2-Benzoylphenyl)amino]-2-{4-[2-(5-methyl-2-phenyloxazol-4-yl)ethoxy]phenyl}ethyl}}-5-cyclopropyl-1,3,4-oxadiazole To a stirred solution of the intermediate (2S)-[(2-benzoylphenyl)amino]-3-{4-[2-(5-methyl-2-phenyloxazol- 4-yl)ethoxy]phenyl}propionic hydrazide described in Example 1 (158 mg, 0.28 mmol) in, CH$_2$Cl$_2$ (5 mL) was added 4-methylmorpholine (37 mg, 0.37 mmol) followed by cyclopropanecarbonyl chloride (35 mg, 0.33 mmol). The resulting gelatinous mixture was stirred overnight and filtered. The collected solid material was washed with hexane followed by a minimal amount of CH$_2$Cl$_2$ and dried in vacuo to afford the desired diacyl hydrazide (165 mg, 94%) as a yellow solid.

The above diacyl hydrazide (140 mg, 0.22 mmol) was cyclized as described in Example 5 to provide the desired 1,3,4-oxadiazole (66 mg, 49%) as a yellow foam. Low resolution MS (ES$^+$) m/e 611 (MH$^+$); 400 MHz $^1$H NMR (CDCl$_3$) δ 8.94 (d, 1H), 7.97 (m, 2H), 7.59–7.30 (m, 10H), 7.12 (d, 2H), 6.86 (d, 1H), (d, 2H), 6.60 (t, 1H), 5.05 (m, 1H), 4.18 (t, 2H), 3.27 (d, 2H), 2.94 (t, 2H), 2.35 (s, 3H), 2.07 (m, 1H), 1.27 (m, 2H), 1.08 (m, 2H).

Example 8

(S)-{{5-[1-(2-Benzoylphenyl)amino]-2-{4-[2-(5-methyl-2-phenyloxazol-4-yl)ethoxy]phenyl}ethyl}}-3-methyl-1,2,4-oxadiazole To a stirred, cooled (0° C.) solution of (2S)-[(2-benzoylphenyl)amino]-3-{4-[2-(5-methyl-2-phenyloxazol-4-yl)ethoxy]phenyl}propionic acid referenced in Example 1 (254 mg, 0.46 mmol) in CH$_2$Cl$_2$ (5 mL) was added 1,3-dicyclohexylcarbodiimide (50 mg, 0.24 mmol). After 1h, the mixture was filtered and evaporated to dryness under reduced pressure. The remaining residue was dissolved in pyridine (2 mL) and a solution of acetamidoxime [prepared as described in Bedford, C. D. et al.; *J. Med. Chem.*, (1986), Vol. 29, 2174–2183] (14.5 mg, 0.20 mmol) in pyridine (1 mL) was added dropwise. The mixture was heated to reflux and left overnight. After cooling to room temperature, the mixture was diluted with CH$_2$Cl$_2$, washed with 1 N aqueous HCl, brine and dried over MgSO$_4$. Solvent was removed under reduced pressure and the resulting residue was chromatographed on silica gel eluting with 1:9 EtOAc in hexane followed by 1:3 EtOAc in hexane to provide the desired 1,2,4-oxadiazole (20 mg, 17%) as a yellow foam. Low resolution MS (ES$^+$) m/e 585 (MH$^+$).

Example 9

(S)-{{5-[1-(2-Benzoylphenyl)amino]-2-{4-[2-(5-methyl-2-phenyloxazol-4-yl)ethoxy]phenyl}ethyl}}-3-propyl-1,2,4-oxadiazole To a stirred solution of (2S)-[(2-benzoylphenyl)amino]-3-{4-[2-(5-methyl-2-phenyloxazol-4-yl)ethoxy]phenyl}propionic acid referenced in Example 1 (498 mg, 0.91 mmol) in CH$_2$Cl$_2$ (15 mL) was added 1-hydroxybenzotriazole (122 mg, 0.90 mmol) and 1-(3-dimethylaminopropyl)-3-ethylcarbodiimide hydrochloride (173 mg, 25 0.90 mmol) followed by 4-methylmorpholine (230 mg, 2.27 mmol). The mixture was stirred for 5 minutes and then a solution of butanamidoxime (124 mg, 1.21 mmol) in CH$_2$Cl$_2$ (10 mL) was added. The mixture was stirred overnight, diluted with CH$_2$Cl$_2$, washed with water, brine and dried over MgSO$_4$. Solvent was removed under reduced pressure and the resulting residue was chromatographed on silica gel eluting with 2:1 EtOAc in hexane to afford the desired acyl amidoxime (423 mg, 76%) as a yellow solid.

The above acyl amidoxime (185 mg, 0.29 mmol) was placed in a reuseable thick walled pressure tube and suspended in p-xylene (1 mL) with stirring. The reaction vessel was sealed, placed in an oil bath preheated to 125° C. and left overnight. After cooling to room temperature, the mixture was transferred to a column of silica gel and eluted with 1:9 EtOAc in hexane followed by 15:85 EtOAc in hexane. Further purification on silica gel using radial chromatography provided the desired 1,2,4-oxadiazole (95 mg, 53%) as a yellow glass. Low resolution MS (ES$^+$) m/e 635 (MH$^+$); 300 MHz $^1$H NMR (CDCl$_3$) δ 9.05 (d, 1H), 7.97 (m, 2H), 7.61–7.31 (m, 10H), 7.11 (d, 2H), 6.79 (d, 2H), 6.71 (d, 1H), 6.60 (t, 1H), 5.06 (m, 1H), 4.18 (t, 2H), 3.33 (d, 2H), 2.94 (t, 2H), 2.67 (t, 2H), 2.35 (s, 3H), 1.73 (m, 2H) 0.93 (t, 3H); Anal. Calc'd. for C$_{38}$H$_{36}$N$_4$O$_4$.0.25 H$_2$O: C, 73.95; H, 5.96; N, 9.08. Found: C, 73.67; H, 5.90; N, 8.97.

Example 10

(S)-{5-[1-(2-Benzoylphenyl)amino]-2-{4-[2-(5-methyl-2-phenyloxazol-4-yl)ethoxylphenyl}ethyl}}-3-methoxymethyl-1,2,4-oxadiazole Prepared from (2S)-[(2-benzoylphenyl)amino]-3-{4-[2-(5-methyl-2-phenyloxazol-4-yl)ethoxy]phenyl}propionic acid referenced in Example 1 and methoxyacetamidoxime to provide the desired 1,2,4-oxadiazole (31%) as a yellow foam. Low resolution MS (ES$^+$) m/e 615 (MH$^+$); 400 MHz $^1$H NMR (CDCl$_3$) δ 9.06 (d, 1H), 7.97 (m, 2H), 7.60–7.29 (m, 10H), 7.13 (d, 2H), 6.80 (d, 2H), 6.69 (d, 1H), 6.60 (t, 1H), 5.10 (m, 1H), 4.55 (s, 2H), 4.18 (t, 2H), 3.49 (s, 3H), 3.35 (m, 2H), 2.95 (t, 2H), 2.35 (s, 3H); Anal. Calc'd. for C$_{37}$H$_{34}$N$_4$O$_5$.0.50 H$_2$O: C, 71.25 H, 5.66; N, 8.98. Found: C, 71.00; H, 5.67; N, 8.61.

Example 11

(S)-{{5-[1-(2-Benzoylphenyl)amino]-2-{4-[2-(5-methyl-2-phenyloxazol-4-yl)ethoxy]phenyl}ethyl}}-3-ethyl-1,2,4-oxadiazole Prepared from (2S)-[(2-benzoylphenyl)amino]-3-{4-[2-(5-methyl-2-phenyloxazol-4-yl)ethoxy]phenyl}propionic acid referenced in Example 1 and propanamidoxime to provide the desired 1,2,4-oxadiazole (45%) as a yellow foam. Low resolution MS (ES$^+$) m/e 599 (MH$^+$); 300 MHz $^1$H NMR (CDCl$_3$) δ 9.05 (d, 1H), 7.97 (m, 2H), 7.60–7.29 (m, 10H), 7.12 (d, 2H), 6.80 (d, 2H), 6.69 (d, 1H), 6.60 (t, 1H), 5.06 (m, 1H), 4.17 (t, 2H), 3.33 (d, 2H), 2.94 (t, 2H), 2.74 (q, 2H) 2.34 (s, 3H), 1.30 (t, 3H).

Example 12

(S)-{{2-[1-(2-Benzoylphenyl)amino]-2-{4-[2-(5-methyl-2-phenyloxazol-4-yl)ethoxy]phenyl}ethyl}}-5-isopropyl-1,3,4-thiadiazole To a stirred solution of (2S)-[(2-benzoylphenyl)amino]-3-{4-[2-(5methyl-2-phenyloxazol-4-yl)ethoxy]phenyl}propionic acid referenced in Example 1 (501 mg, 0.92 mmol) in CH$_2$Cl$_2$ (10 mL) was added isobutyric acid hydrazide (112 mg, 1.10 mmol), 1-hydroxybenzotriazole (136 mg, 1.01 mmol) and triethylamine (233 mg, 2.30 mmol). The mixture was stirred for 5 min and then 1-(3-dimethylaminopropyl)3-ethylcarbodiimide hydrochloride (0.211 g, 1.101 mmol) was added. A yellow precipitate formed. After stirring overnight, the mixture was filtered and the collected solid was dried in vacuo to afford the desired diacyl hydrazide (1.29 g, 100%) as a yellow solid.

The above diacyl hydrazide (261 mg, 0.36 mmol) and Lawesson's Reagent (290 mg, 0.72 mmol) in toluene (5 mL) were refluxed for 4h. After cooling to room temperature, the mixture was concentrated and chromatographed on silica gel eluting with EtOAc in hexane (1:10 to 1:1). The isolated semipurified material was then charged to a basic alumina column and eluted with 100:1 $CH_2Cl_2$—MeOH to provide the desired 1,3,4-thiadiazole (62 mg, 27%) as a red-brown foam. Low resolution MS ($ES^+$) m/e 628 ($MH^+$); 400 MHz $^1H$ NMR ($CDCl_3$) δ 9.04 (d, 1H), 7.90 (dd, 2H), 7.52 (d, 2H), 7.48 (d, 1H), 7.40–7.30 (m, 7H), 7.25 (d, 2H), 6.75 (d, 2H), 6.65 (d, 1H), 6.50 (t, 1H), 5.15 (m, 1H), 4.10 (t, 2H), 3.35–3.10 (m, 3H), 2.9 (t, 2H), 2.35 (s, 3H), 1.32 (t, 6H).

Example 13

(S)-{{2-[1-(2-Benzoylphenyl)amino]-2-{4-[2-(5-methyl-2-phenyloxazol-4-yl)ethoxy]phenyl}ethyl}}-5-propyl-1,3,4-thiadiazole Prepared from (2S)-[(2-benzoylphenyl)amino]-3-{4-[2-(5-methyl-2-phenyloxazol-4-yl)ethoxy]phenyl}propionic acid referenced in Example 1 and butyric acid hydrazide. Cyclization provided the desired 1,3,4-thiadiazole. Low resolution MS ($ES^+$) m/e 629 ($MH^+$); 400 MHz $^1H$ NMR ($CDCl_3$) δ 9.50 and 8.88 (d, 1H, rotamers), 7.80 (bd, 2H), 7.60–7.40 (m, 10H), 7.20–7.05 (m, 2H), 6.95–6.75 (m, 3H), 6.65–6.55 (m, 1H), 5.50 and 5.40 (q, 1H rotamers), 4.25 (m, 2H), 3.30–3.15 (m, 2H), 2.90 (t, 2H), 2.90–2.80 (m, 2H), 2.3 (s, 3H), 1.65 (p, 2H), 0.85 (t, 3H).

Example 14

(S)-{{2-[1-(2-Benzoylphenyl)amino]-2-{4-[2-(5-methyl-2-phenyloxazol-4-yl)ethoxy]phenyl}ethyl}}-5-methyl-1,3,4-thiadiazole Prepared from (2S )-[(2-benzoylphenyl)amino]-3-{4-[2-(5-methyl-2-phenyloxazol-4-yl)ethoxy]phenyl}propionic acid referenced in Example 1 and propionic acid hydrazide. Cyclization provided the desired 1,3,4-thiadiazole. Low resolution MS ($ES^+$) m/e 601 ($MH^+$); 400 MHz $^1H$ NMR ($CDCl_3$) δ 9.06 (d, 1H), 7.90 (dd, 2H), 7.62–7.38 (m, 10H), 7.20 (d, 2H), 6.82 (d, 2h), 6.70 (d, 1H), 6.58 (t, 1H), 5.2 (m, 1H), 4.18 (t, 2H), 3.42–3.25 (m, 2H), 2.9 (t, 2H), 2.7 (s, 3H) (s, 3H).

Example 15

(S)-{{2-[1-(2-Benzoylphenyl)amino]-2-{4-[2-(5-methyl-2-phenyloxazol-4-yl)ethoxy]phenyl}ethyl}}-5-methyl-1,3,4-triazole To a stirred, cooled (0° C.) solution of the intermediate (2S)-[(2-benzoylphenyl)amino]-3-{4-[2-(5-methyl-2-phenyloxazol-4-yl)ethoxy]phenyl}propionic hydrazide described in Example 1 (197 mg, 0.35 mmol) in THF (5 mL) was added ethyl acetimidate hydrochloride (51 mg, 0.41 mmol) followed by triethylamine (47 mg, 0.47 mmol). After 1.5 h, the mixture was allowed to warm to room temperature and stir overnight. Removal of solvent under reduced pressure gave a residue which was dissolved in EtOAc, washed with saturated aqueous $NaHCO_3$, brine and dried over $MgSO_4$. Solvent was removed under reduced pressure and the remaining residue was chromatographed on silica gel eluting with EtOAc followed by 5:95 MeOH in $CH_2Cl_2$ to afford the desired acyl amidrazo e (153 mg, 73%) as a yellow foam.

The above acyl amidrazone (150 mg, 0.25 mmol) was placed in a reuseable thick walled pressure tube and suspended in p-xylene (1.5 mL) with stirring. The reaction vessel was sealed, placed in an oil bath heated to 120° C. and left overnight. After cooling to room temperature, the mixture was transferred to a column of silica gel and eluted with 1:1 EtOAc in hexane followed by 3:2 EtOAc in hexane. Further purification on silica gel using radial chromatography provided the desired 1,2,4-triazole (103 mg, 71%) as a yellow solid. Low resolution MS ($ES^+$) m/e 584 ($MH^+$); 400 MHz $^1H$ NMR ($CDCl_3$) δ 8.92 (d, 1H), 7.96 (m, 2H), 7.58–7.31 (m, 10H), 7.10 (d, 2H), 6.78 (d, 2H), 6.63 (d, 1H), 6.55 (t, 1H), 4.95 (m, 1H), 4.13 (m, 2H), 3.33 (m, 1H), 3.20 (m, 1H), 2.93 (m, 2H), 2.50 (s, 3H), 2.34 (s, 3H).

Example 16

(S)-{{2-[1-(2-Benzoylphenyl)amino]-2-{4-[2-(5-methyl-2-15 phenyloxazol-4-yl)ethoxy] phenyl}ethyl}}-5-propyl-1,3,4-triazole Prepared by the method described in Example 15 from the intermediate (2S)-[(2-benzoylphenyl)amino]-3-{4-[2-(5-methyl-2-phenyloxazol-4-yl)ethoxy]phenyl}propionic hydrazide described in Example 1 (207 mg, 0.37 mmol) and ethyl butyrimidate hydrochloride (68 mg, 0.45 mmol). Cyclization provided the desired 1,3,4-triazole (78%) as a yellow foam. Low resolution MS ($ES^+$) m/e 612 ($MH^+$); 300 MHz $^1H$ NMR ($CDCl_3$) δ 8.92 (d, 1H), 7.96 (m, 2H), 7.59–7.39 (m, 10H), 7.09 (d, 2H), 6.77 (d, 2H), 6.65 (d, 1H), 6.56 (t, 1H), 4.97 (m, 1H), 4.16 (t, 2H), 3.28 (m, 2H), 2.93 (t, 2H), 2.74 (t, 2H), 2.34 (s, 3H), 1.80 (m, 2H), 0.98 (s, 3H); Anal. Calc'd. for $C_{39}H_{37}N_5O_3 \cdot 0.5\ H_2O$: C, 73.53; H, 6.17; N, 11.28. Found: C, 73.88; H, 6.35; N, 10.91.

Example 17

(S)-{{2-[1-(2-Benzoylphenyl)amino]-2-{4-[2-(5-methyl-2-phenyloxazol-4-yl)ethoxy]phenyl}ethyl}}-4-ethyl-1,3-oxazole To a stirred solution of (2S)-[(2-benzoylphenyl)amino]-3-{4-12-(5-methyl-2-phenyloxazol-4-yl)ethoxy]phenyl}propionic acid referenced in Example 1 (501 mg, 0.92 mmol) in $CH_2Cl_2$ (30 mL) was added 2-aminobutanol (273 mg, 3.06 mmol), 1-hydroxybenzotriazole (414 mg, 3.06 mmol) and triethylamine (511 mg, 5.05 mmol). The mixture was stirred for 5 min and then 1-(3-dimethylaminopropyl)-3-ethylcarbodiimide hydrochloride (640 mg, 3.34 mmol) was added. After stirring overnight, the mixture was diluted with $CH_2Cl_2$, washed with water, dried over $MgSO_4$, filtered and concentrated. The crude material was chromatographed on silica gel eluting with 40:1 $CH_2Cl_2$ in MeOH to afford the desired amide (1.32 g, 77%) as a yellow solid.

A solution of the above amide (1.32 g, 2.14 mmol) and 4-methylmorpholine (1.00 g, 8.56 mmol) in $CH_2Cl_2$ was dried over $MgSO_4$ and filtered. Celite (0.50 g) was added to the solution and after stirring for 5 minutes, the mixture was treated with TPAP (0.188 g, 0.535 mmol). The reaction was stirred for 5 min and then filtered through a pad consisting of 3" of celite on top of 3" of silica eluting with $CH_2Cl_2$. Removal of solvent under reduced pressure afforded the desired aldehyde (247 mg, 19%).

A solution of iodine (203 mg, 0.80 mmol), triphenylphosphine (210 mg, 0.80 mmol) and triethylamine (162 mg, 1.60 mmol) in $CH_2Cl_2$ (5 mL) was stirred for 5 minutes. To this mixture was added a solution of the above aldehyde (247 mg, 0.40 mmol) in $CH_2Cl_2$ (5 mL). After stirring for 1.5 h, the mixture was poured into a saturated solution of $Na_2S_3O_3$. The layers were separated and the aqueous layer was further extracted with diethyl ether. The combined organic layers were dried over $MgSO_4$, filtered and concentrated under reduced pressure. Purification of the crude material by chromatography on silica gel eluting with 3:1 EtOAc in hexane provided the desired oxazole (40 mg, 17%). Low resolution MS (ES$^+$) m/e 620 (M+Na);400 MHz $^1$H NMR (CDCl$_3$) δ 8.97 (d, 1H), 7.92 (d, 2H), 7.59 (d, 2H), 7.5 (t, 1H), 7.44–7.39 (m, 7H), 7.29 (t, 1H), 7.02 (d, 2H), 6.71 (d, 3H), 6.48 (t, 1H), 4.84 (q, 1H), 4.12 (t, 2H), 3.21 (t, 2H), 2.90 (t, 2H), 2.46 (q, 2H), 2.29 (s 3H), 1.98 (t, 3H).

Example 18

(S){{2-[1-(2-Benzoylphenyl)amino]-2-{4-[2-(5-methyl-2-phenyloxazol-4-yl)ethoxy]phenyl}ethyl}}-4-isopropyl-1,3-oxazole Prepared from (2S)-[(2-benzoylphenyl)amino]-3-{4-[2-(5-methyl-2-phenyloxazol-4-yl)ethoxy]phenyl}propionic acid referenced in Example 1 and valinol. TPAP oxidation and cyclization provided the desired oxazole. Low resolution MS (ES$^+$) m/e 612 (MH$^+$); 400 MHz $^1$H NMR (CDCl$_3$) 69.02 (d, 1H), 7.96 (dd, 2H), 7.59 (d, 2H), 7.49 (d, 1H), 7.44–7.39 (m, 6H), 7.29 (t, 1H), 7.2 (s, 1H), 7.07 (d, 2H), 6.79 (dd, 3H), 6.54 (t, 1H), 4.91 (q, 1h), 4.18 (t, 2H), 3.26 (t, 2H), 2.93 (t, 2H), 2.79 (p, 1H), 2.35 (s, 3H), 1.98 (dd, 6H). Anal. Calc'd. for $C_{39}H_{37}N_3O_4$: C, 76.57; H, 6.10; N, 6.87; Found C, 76.82; H, 6.24; N, 6.66.

Example 19

(S){{2-[1-(2-Benzoylphenyl)amino]-2-4-[2-(5-methyl-2-phenyloxazol-4-yl)ethoxy]phenyl}ethyl}}-4-propyl-1,3-oxazole Prepared from (2S)-[(2-benzoylphenyl)amino]-3-{4-[2-(5-methyl-2-phenyloxazol-4-yl)ethoxy]phenyl}propionic acid referenced in Example 1 and 2-aminopentanol. TPAP oxidation and cyclization provided the desired oxazole. Low resolution MS (ES$^+$) m/e 612 (MH$^+$); 400 MHz $^1$H NMR (CDCl$_3$) δ 9.02 (d, 1H), 7.97 (dd, 2H), 7.59 (d, 2H),. 7.52–7.39 (m, 9H), 7.29 (t, 1H), 7.07 (d, 2H), 6.78 (dd, 3H), 6.54 (t, 1H), 4.91 (q, 1 h), 4.18 (t, 2H), 3.26 (dd, 2H), 2.93 (t, 2H), 2.45 (t, 2H) 2.42(s, 3H), 0.90 (t, 3H).

Example 20

(S)-{{2-[1-(2-Benzoylphenyl)amino]-2-{4-[2-(5-methyl-2-phenyloxazol-4-yl)ethoxy]phenyl}ethyl}}-4-propyl-1,3-oxazole Prepared from (2S)-[(2-benzoylphenyl)amino]-3-{4-[2-(5-methyl-2-phenyloxazol-4-yl)ethoxy]phenyl}propionic acid referenced in Example 1 and serine methyl ester. Oxidation by the method of Swern [Mancuso, A. J.; Huang, S. L.; Swern, D. J. Org. Chem., (1978), Vol.43, 2480–2482] and cyclization provided the desired oxazole (50%). Low resolution MS (ES$^+$) m/e 628 (MH$^+$); 400 MHz $^1$H NMR (CDCl$_3$) δ 9.04 (d, 1H), 7.96 (dd, 2H), 7.60–7.27 (m, 13H), 7.11 (d, 2H), 6.81–6.75 (m, 4H), 6.57 (t, 1H), 5.03 (q, 1H), 4.19 (t, 2H), 3.91 (s, 3H), 3.31 (t, 2H), 2.94 (t, 2H).

Binding Assay

Test compounds were assayed for binding to the human PPAR-gamma receptor ligand binding domain as described in Nichols, J. S., Parks, D. J., Consler, T. G., and Blanchard, S. G., Anal. Biochem., (1998), Vol. 257, pp 112–119. Each of the above Examples 1–20 had a $pK_i$>5 in this binding assay.

Representative binding assays for PPAR-alpha and PPAR-delta are described in Xu et al, Mol. Cell (1999), Vol. 3, pp 397–403.

Cell-based Reporter Assay

CV-1 cells were maintained in DME High Glucose medium (Irvine Scientific) supplemented with 10% fetal bovine serum and 2 mM Glutamine. Cells were split into D-MEM/F-12 medium (Gibco) supplemented with 10% charcoal stripped fetal bovine serum for 3 d before harvesting. Cells were harvested into D-MEM/F-12 medium (Gibco) supplemented with 10% charcoal stripped fetal bovine serum and counted. Cells were seeded at a density of 24,000 cells per well into 96-well plates and incubated overnight at 5% $CO_2$ and 37° C. Cells were transfected for 6 to 20 hours based on the Lipofectamine protocol (Gibco) with the following amounts of DNA per well: 2 ng PSG5 GAL4-human PPAR-gamma, 8 ng UAS-tk-SPAP, 25 ng beta-gal, 45 ng pBluescript. See Lehmann, J. M. et al., J. Biol. Chem., (1995), Vol. 270, pp 12953–12956 and Brown, P. J. et al., Chem. Biol., (1997), Vol. 4, pp 909–918. Cells were incubated overnight at 5% CO2 and 37° C. Test compounds were solublized to 10 mM in DMSO. Test compounds were then serially diluted from 1e-5 M to 1e-10 M into D-MEM/F-12 (Gibco) medium supplemented with 10% delipidated and charcoal stripped calf serum (Sigma) heat inactivated at 60° C. for 30 minutes, 2 mM Glutamine, and Pen-Strep. This medium into which the test compounds were diluted also contained 100 nM rosiglitazone. These test compound dilutions were added 100 microliters/well to the transfected cell plates after the transfection media were aspirated. DMSO controls and 1 micromolar rosiglitazone controls were added to each cell plate. Cells were incubated overnight at 5% $CO_2$ and 37° C. Cells were lysed with 25 microliters 0.5% Triton X-100. Two daughter plates were made from each mother plate. One daughter received 200 microliters/well SPAP substrate (Sigma 104) and the other daughter received 200 microliters/well beta-gal substrate (Sigma N-1127). Once developed, cell plates were read at 405 nM. SPAP data were normalized to beta-gal, and % maximum inhibition of transactivation was calculated relative to the 1 micromolar rosiglitazone positive control. Each of the above Examples 1–20 had >50% inhibition of transactivation by 100 nM rosiglitazone in this PPAR-gamma cell based reporter gene assay.

The PPAR-alpha cell based reporter assay was as described for PPAR-gamma except that it employed GAL4-human PPAR-alpha in place of GAL4-human PPAR-gamma, and 2-(4-(2-(1-Heptyl-3-(4-fluorophenyl)ureido)ethyl)phenoxy)-2-methylpropionic acid in place of rosiglitazone.

The PPAR-delta cell based reporter assay was as described for PPAR-alpha except that it employed GAL4-human PPAR-delta in place of GAL4-human PPAR-alpha, and a 10 fold higher concentration of 2-(4-(2-(1-Heptyl-3-(4-fluorophenyl)ureido)ethyl)phenoxy)2-methylpropionic acid as the agonist.

Adipocyte Differentiation Assay

C3H10T1/2 clone 8 murine fibroblasts (American Type Culture Collection) below passage 22 were maintained in Dulbecco's modified Eagle's medium (Life Technologies, Inc.) supplemented with 10% fetal calf serum and 100 units/mL penicillin G and 100 microgram/mL streptomycin. One day after passage into 96-well microtiter plates (12.5× 103 cells/cm$^2$), the cells were treated with 150 nM rosiglitazone plus 1 micromolar insulin and 1 micromolar 9-cis-retinoic acid (Sigma, St. Louis, Mo.). Vehicle or test compounds, which had been solublized to 10 mM in DMSO and then serially diluted from 1e-5 M to 1e-10 M into medium, were added. After 7 days, cells were lysed in 0.01% Digitonin (Sigma, St. Louis, Mo.) and the lipogenic activity determined by measuring total triglycerides using a Glycerol-Triglyceride (GPO-Trinder) kit (337-B,Sigma, St. Louis, Mo.). The mixture was incubated at 37° C. for 2 h and the absorbance read at 550 nm. The % maximum inhibition of lipogenesis was calculated relative to the vehicle treated cells. Each of the above Examples 1–20 had >50% inhibition of lipogenesis induced by 150 nM rosiglitazone in this adipocyte differentiation assay.

This data suggests that PPAR gamma antagonists of this invention will not cause weight gain or increased adiposity.

Experimental Animal Protocol

Age and weight matched male ZDF/GMI fa/fa rats (Genetic Models) were housed at 72 degF. and 50% relative humidity with a 12 hr light and dark cycle. Starting at 8 weeks of age the animals were dosed twice a day by oral gavage with 150 mg/kg of example 2. After 2 weeks the animals were anesthetized with isofluorane, blood drawn by cardiac puncture, and non-fasting measurements of glucose, triglycerides, and non-esterified free fatty acids (NEFAS) were obtained. The data were calculated as the mean and standard error (SEM) from experiments performed on ten animals per treatment group. Two-tailed tests were performed to calculate P values using Excel on a personal computer. This research complied with the principles of laboratory animal care (NIH publication No. 86–23, revised 1985) and company policy on the care and use of animals and related codes of practice.

| Control | | Example 1 | |
|---|---|---|---|
| Glucose (mg/dL) | 313 ± 62 | 201 ± 13 | (P < 0.05) |
| Triglycerides (mg/dL) | 1507 ± 143 | 734 ± 102 | (P < 0.005) |
| Free Fatty Acids (mEq/L) | 1.48 ± 0.09 | 1.14 ± 0.06 | (P < 0.005) |

These data suggest that PPAR gamma antagonists of this invention may be useful for treatment of diabetes, obesity, metabolic syndrome, impaired glucose tolerance, syndrome X, and cardiovascular diseases including dysplidemia.

What is claimed is:

1. A compound of Formula (I) or (II), or pharmaceutically acceptable salts or solvates thereof,

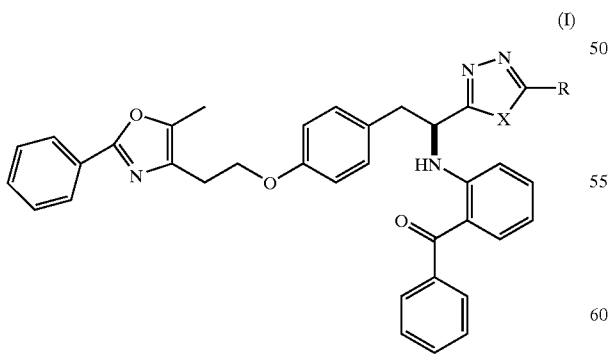

(I)

where in Formula (I) X is O, S, or NH;
and R is methyl, ethyl, n-propyl, i-propyl, cyclopropyl, n-butyl, phenyl, or —CH$_2$OCH$_3$,

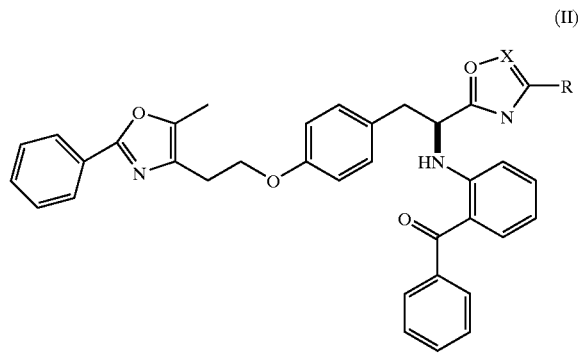

(II)

and where in Formula (II) X is C or N;
and R is methyl, ethyl, n-propyl, i-propyl, —CH$_2$OCH$_3$, or —CO$_2$CH$_3$.

2. A compound of claim 1 wherein said compound is a PPAR gamma antagonist.

3. A compound of claim 2 wherein said compound is selected from the group consisting of:

(S)-{{2-[1-(2-Benzoylphenyl)amino]-2-{4-[2-(5-methyl-2-phenyloxazol-4-yl)ethoxy]phenyl}ethyl}}-5-propyl-1,3,4-oxadiazole, (S)-{{2-[1-(2-Benzoylphenyl)amino]-2-{4-[2-(5-methyl-2-phenyloxazol-4-yl)ethoxy]phenyl}ethyl}}-5-ethyl-1,3,4-oxadiazole, (S)-{{2-[1-(2-Benzoylphenyl)amino]-2-{4-[2-(5-methyl-2-phenyloxazol-4-yl)ethoxy]phenyl}ethyl}}-5-phenyl-1,3,4-oxadiazole, (S)-{{2-[1-(2-Benzoylphenyl)amino]-2-{4-[2-(5-methyl-2-phenyloxazol-4-yl)ethoxy]phenyl}ethyl}}-5-butyl-1,3,4-oxadiazole, (S)-{{2-[1-(2-Benzoylphenyl)amino]-2-{4-[2-(5-methyl-2-phenyloxazol-4-yl)ethoxy]phenyl}ethyl}}-5-methyl-1,3,4-oxadiazole, (S)-{{2-[1-(2-Benzoylphenyl)amino]-2-{4-[2-(5-methyl-2-phenyloxazol-4-yl)ethoxy]phenyl}ethyl}}-5-methoxymethyl-1,3,4-oxadiazole, (S)-{{2-[1-(2-Benzoylphenyl)amino]-2-{4-[2-(5-methyl-2-phenyloxazol-4-yl)ethoxy]phenyl}ethyl}}-5-cyclopropyl-1,3,4-oxadiazole, (S){{5-[1-(2-Benzoylphenyl)amino]-2-{4-[2-(5-methyl-2-phenyloxazol-4-yl)ethoxy]phenyl}ethyl}}-3-methyl-1,2,4-oxadiazole, (S)-{{5-[1-(2-Benzoylphenyl)amino]-2-{4-[2-(5-methyl-2-phenyloxazol-4-yl)ethoxy]phenyl}ethyl}}-3-propyl-1,2,4-oxadiazole, (S)-{{5-[1-(2-Benzoylphenyl)amino]-2-{4-[2-(5-methyl-2-phenyloxazol-4-yl)ethoxy]phenyl}ethyl}}-3-methoxymethyl-1,2,4-oxadiazole, (S)-{{5-[1-(2-Benzoylphenyl)amino]-2-{4-[2-(5-methyl-2-phenyloxazol-4-yl)ethoxy]phenyl}ethyl}}-3-ethyl-1,2,4-oxadiazole, (S)-{{2-[1-(2-Benzoylphenyl)amino]-2-{4-[2-(5-methyl-2-phenyloxazol-4-yl)ethoxy]phenyl}ethyl}}-5-isopropyl-1,3,4-thiadiazole, (S)-{{2-[1-(2-Benzoylphenyl)amino]-2-{4-[2-(5-methyl-2-phenyloxazol-4-yl)ethoxy]phenyl}ethyl}}-5-propyl-1,3,4-thiadiazole, (S)-{{2-[1-(2-Benzoylphenyl)amino]-2-{4-[2-(5-methyl-2-phenyloxazol-4-yl)ethoxy]phenyl}ethyl}}-5-methyl-1,3,4-thiadiazole, (S)-{{2-[1-(2-Benzoylphenyl)amino]-2-{4-[2-(5-methyl-2-phenyloxazol-4-yl)ethoxy]phenyl}ethyl}}-5-methyl-1,3,4-triazole, (S)-{{2-[1-(2-Benzoylphenyl)amino]-2-{4-[2-(5-methyl-2-phenyloxazol-4-yl)ethoxy]phenyl}ethyl}}-5-propyl-1,3,4-triazole, (S)-{{2-[1-(2-Benzoylphenyl)amino]-2-{4-[2-(5-methyl-2-phenyloxazol-4-yl)ethoxy]phenyl}ethyl}}-4-ethyl-1,3-oxazole, (S)-{{2-[1-(2-Benzoylphenyl)amino]-2-{4-[2-(5-methyl-2-phenyloxazol-4-yl)ethoxy]phenyl}ethyl}}-4-isopropyl-1,3-oxazole, (S)-{{2-[1-(2-Benzoylphenyl)amino]-2-{4-[2-(5-methyl-2-phenyloxazol-4-yl)ethoxy]phenyl}ethyl}}-4-propyl-1,3-oxazole, (S) {{2-[1-(2-Benzoylphenyl)amino]-2-{4-[2-(5-methyl-2-phenyloxazol-4-yl)ethoxy]phenyl}ethyl}}-4-methoxycarbonyl-1,3-oxazole, and pharmaceutically acceptable salts and solvates thereof.

4. A compound of claim 2 wherein said compound is selected from the group consisting of (S)-{{2-[1-(2-Benzoylphenyl)amino]-2-{4-[2-(5-methyl-2-phenyloxazol-4-yl)ethoxy]phenyl}ethyl}}-5-propyl-1,3,4-oxadiazole and pharmaceutically acceptable salts and solvates thereof.

5. A method for prevention or treatment of a PPAR-gamma mediated disease or condition comprising administration of a therapeutically effective amount of a compound of claim 2.

6. The method of claim 5 wherein said disease or condition is selected from the group consisting of diabetes, obesity, metabolic syndrome, impaired glucose tolerance, syndrome X, and cardiovascular diseases.

7. The method of claim 5 wherein said disease of condition is selected from the group consisting of diabetes and cardiovascular diseases.

* * * * *

UNITED STATES PATENT AND TRADEMARK OFFICE
CERTIFICATE OF CORRECTION

PATENT NO. : 6,506,781 B1 Page 1 of 1
DATED : January 14, 2003
INVENTOR(S) : Jeffrey Edmond Cobb and Barry George Shearer It is certified that error appears in the above-identified patent and that said Letters Patent is hereby corrected as shown below:

<u>Title page,</u>
Item [75], Inventors, should read:
 -- [75] Inventors: Jeffrey Edmond Cobb, Durham NC (US);
 Barry George Shearer, Durham, NC (US) --

Signed and Sealed this

Ninth Day of December, 2003

JAMES E. ROGAN
*Director of the United States Patent and Trademark Office*